US011806450B2

(12) United States Patent
Du et al.

(10) Patent No.: US 11,806,450 B2
(45) Date of Patent: Nov. 7, 2023

(54) AIR STERILIZING DEVICE

(71) Applicants: Guodong Du, Guangdong (CN); Monagas Asensio Pedro, Guangdong (CN)

(72) Inventors: Guodong Du, Guangdong (CN); Monagas Asensio Pedro, Guangdong (CN)

( * ) Notice: Subject to any disclaimer, the term of this patent is extended or adjusted under 35 U.S.C. 154(b) by 306 days.

(21) Appl. No.: 17/238,280

(22) Filed: Apr. 23, 2021

(65) Prior Publication Data
US 2021/0236683 A1    Aug. 5, 2021

Related U.S. Application Data

(63) Continuation of application No. PCT/CN2018/112481, filed on Oct. 29, 2018.

(51) Int. Cl.
*F24F 8/40* (2021.01)
*A61L 9/12* (2006.01)
(Continued)

(52) U.S. Cl.
CPC .............. *A61L 9/205* (2013.01); *A61L 9/046* (2013.01); *A61L 9/122* (2013.01); *A61L 9/145* (2013.01);
(Continued)

(58) Field of Classification Search
CPC .......... A61L 9/046; A61L 9/122; A61L 9/127; A61L 9/145; A61L 9/16; A61L 9/205;
(Continued)

(56) References Cited

U.S. PATENT DOCUMENTS 11,191,862 B2*  12/2021  Yim ..................... A61L 9/015
2004/0217188 A1*  11/2004  McEwen ............. A01M 1/2083
239/44
(Continued)

FOREIGN PATENT DOCUMENTS

CN       102105403 A     6/2011
CN       201995535 U    10/2011
(Continued)

OTHER PUBLICATIONS

Korean Office Action in response to Application No. 10-2019-70200039 (Year: 2020).*
(Continued)

*Primary Examiner* — Jennifer Wecker
*Assistant Examiner* — Brady C Pilsbury (57) ABSTRACT

An air sterilizing device, comprising: a housing (100), forming an air flow path thereon; an ozone generating unit (200), generating ozone particles to be supplied to the air flow path; a filter cartridge (300), receiving ozone generated by the ozone generating unit (200) to discharge bubbles comprising ozone and hydroxyl radicals; an ultrasonic generating unit (400), connected to the filter cartridge (300) to generate ultrasonic waves; an air supply fan (500), configured to supply air to the air flow path of the housing (100); and a power supply unit, configured to supply power for driving the ozone generating unit (200), the ultrasonic generating unit (400), and the air supply fan (500).

11 Claims, 5 Drawing Sheets

(51) Int. Cl.
- *A61L 9/04* (2006.01)
- *B01D 53/88* (2006.01)
- *A61L 9/20* (2006.01)
- *B01D 53/00* (2006.01)
- *B01D 53/78* (2006.01)
- *B01D 53/79* (2006.01)
- *F24F 3/16* (2021.01)
- *A61L 9/14* (2006.01)
- *A61L 101/02* (2006.01)

(52) U.S. Cl.
CPC ........... *B01D 53/007* (2013.01); *B01D 53/78* (2013.01); *B01D 53/79* (2013.01); *B01D 53/885* (2013.01); *F24F 3/16* (2013.01); *F24F 8/40* (2021.01); *A61L 2101/02* (2020.08); *A61L 2209/12* (2013.01); *A61L 2209/132* (2013.01); *A61L 2209/135* (2013.01); *A61L 2209/14* (2013.01); *B01D 2251/104* (2013.01); *B01D 2251/106* (2013.01); *B01D 2255/20707* (2013.01); *B01D 2255/802* (2013.01); *B01D 2259/804* (2013.01); *B01D 2259/816* (2013.01)

(58) Field of Classification Search
CPC ............. A61L 2101/02; A61L 2209/12; A61L 2209/132; A61L 2209/134; A61L 2209/135; A61L 2209/14; A61L 2209/212; B01D 53/007; B01D 53/78; B01D 53/79; B01D 53/8668; B01D 53/885; B01D 2251/104; B01D 2251/106; B01D 2255/20707; B01D 2255/802; B01D 2257/302; B01D 2257/404; B01D 2257/501; B01D 2257/91; B01D 2258/06; B01D 2259/4508; B01D 2259/804; B01D 2259/816; F24F 3/16; F24F 8/10; F24F 8/22; F24F 8/26; F24F 8/40; Y02A 50/20
See application file for complete search history.

(56) References Cited

U.S. PATENT DOCUMENTS

| | | | | |
|---|---|---|---|---|
| 2008/0289971 | A1* | 11/2008 | Shigihara | A61L 2/035 205/687 |
| 2014/0079597 | A1* | 3/2014 | Segura Rius | A61L 9/015 422/123 |

FOREIGN PATENT DOCUMENTS

| | | | |
|---|---|---|---|
| CN | 103561778 A | | 2/2014 |
| GB | 2406275 A | | 3/2005 |
| JP | 2002282346 A | | 10/2002 |
| KR | 20110004617 A | * | 1/2011 |
| KR | 101600833 B1 | * | 3/2016 |

OTHER PUBLICATIONS

International Search Report of PCT Patent Application No. PCT/CN2018/112481 dated Aug. 1, 2019.

* cited by examiner

AIR STERILIZING DEVICE

CROSS REFERENCE TO RELATED APPLICATIONS

The present application is a Continuation Application of PCT Application No. PCT/CN2018/112481 filed on Oct. 29, 2018, the contents of which are incorporated herein by reference in their entirety.

TECHNICAL FIELD

The disclosure relates to an air sterilizing device with a hydroxyl radical generating device. To be specific, the air sterilizing device possesses the optimum condition of generating a hydroxyl radical (·OH) to generate the maximum amount of the hydroxyl radical within unit time, so as to most effectively remove carbon monoxide, sulfur dioxide, nitrogen dioxide and other air pollutants or bacteria in the air.

BACKGROUND

With the development of industrialization and the intensification of urbanization and population concentration, pollution of the air for people to breathe in becomes increasingly serious. Fossil fuels that people use every day inevitably exhausts pollutants harmful to human beings into the air, and a concentration of pathogenic micro substances such as viruses or bacteria in the air also becomes higher, resulting in that people are increasingly desirable to breathe in clean air. To satisfy this desire, an air purifier or an air sterilizing device needs to be used.

The polluted air contains volatile organic compounds (VOCs), and meanwhile mildew (superfine bacteria) is adsorbed to these VOCs, while bacteria as single-celled organisms usually inhabit moist environments. If people breathe in the air contaminated with the VOCs and spores produced by bacteria and mildew, it will become the cause of various diseases. Bacteria and mildew may cause hypersensitivity and lead to systemic infections. The cell walls of bacteria and mildew protect them against external physical-chemical attacks.

Mildew or yeast is resistant to germicidal mixtures between Gram-positive bacteria and Gram-negative bacteria. Similarly, pillbug with crustacea exoskeletons is harmful to human beings by dwelling in polluted environments and becoming indoor fine dust. Fine dust of pillbug has been a subject of biological study for centuries, and more than 30,000 species have been identified so far.

Most of the pollutants in the air are breathed in by human beings and become the root cause of various diseases, and it is currently known that hydroxyl radicals have the most important effect in the natural purification process of pollutants and serve as a main cleansing agent for eliminating carbon monoxide, sulfur dioxide, nitrogen dioxide and other pollutants in the atmosphere. The hydroxyl radicals in nature exist in the air at a density of 200 to 20 millions (based on per 1 cc air per second).

In general, air purifiers and sterilizing devices widely used at present are generally divided into the following categories.

The first method includes the steps of inhaling air from a purified object space, making the air pass through a filter and absorbing or decomposing pollutants in the air by the filter, which is the most common method. In the case of long-term use of this method, it is necessary to regularly replace the filter with a new one, such maintenance management is necessary, but due to the incomplete characteristics of the filter, the air purification capacity is not highly reliable by the method.

The second method is the method of using an ion generator to increase the ion concentration in the air. Air purifiers that adopt the method at present only produce anions. Although the effect of purification and sterilization by anions can reach a certain level, it is impossible to accurately gauge anion discharge. Moreover, the effect of powerfully removing planktonic bacteria in the air is not good.

The third method is the method that uses a Plasma Cluster Ion (PCI) technology. In this case, harmful substances are decomposed or inactivated by using a plasma ion air purification technology of plasma charges, namely by discharging anions and cations into the air and making the anions and cations chemically react with the harmful substances in the air, thereby purifying the air.

However, a chemical principle of activities of plasma cluster ions in the air purification process in this way has not yet been accurately verified so far. Furthermore, an ion yield may not be accurately analyzed, and therefore the sterilization effect is low in reliability. So far, positive effects and adverse effects have not been fully verified in terms of microbiology.

There are representative existing technical literatures as follows in the field of air sterilizing devices.

UK Patent Bulletin Gazette No. GB 2406275 A (30 Mar. 2005)

Japanese Laid-Open Patent Publication Gazette No. JP 2002-282346 A (2 Oct. 2002)

SUMMARY

The disclosure provides an air sterilizing device for most effectively removing carbon monoxide, sulfur dioxide, nitrogen dioxide and other air pollutants or bacteria in the air by obtaining a generation structure with the optimum condition of generating the hydroxyl radicals and then generating the maximum amount of the hydroxyl radicals within unit time.

The air sterilizing device of one embodiment of the disclosure comprises: a housing, forming an air flow path thereon; an ozone generating unit, generating ozone particles to be supplied to the air flow path; a filter cartridge, receiving ozone generated by the ozone generating unit to discharge bubbles containing ozone and hydroxyl radicals; an ultrasonic generating unit, connected to the filter cartridge to generate ultrasonic waves; an air supply fan, configured to supply air to the air flow path of the housing; and a power supply unit, configured to supply power for driving the ozone generating unit, the ultrasonic generating unit and the air supply fan.

The housing comprises: the first flow path, configured to guide the air supplied by the air supply fan; a second flow path, configured to guide gas in the bubbles generated by a solution in the filter cartridge; and a third flow path, configured to mix the air flowing in the first flow path with the gas in the second flow path.

The air sterilizing device of one embodiment of the disclosure further comprises: a photocatalysis substance, coated on at least one of the second flow path and the third flow path; and a light source, configured on the second flow path to illuminate the photocatalysis substance by ultraviolet light of less than 390 nm.

The air sterilizing device of one embodiment of the disclosure further comprises a pump connected with the ozone generating unit and configured to supply part of ozone to the filter cartridge.

The pump only works for periods of time in the working process of the ozone generating unit, that is, the pump only works for 5 min to 10 min every hour.

The filter cartridge of the air sterilizing device of one embodiment of the disclosure comprises: a tank, configured to contain the solution; a diffusion pipe, connected with the pump and configured to supply the ozone into the solution; and an evaporation part, configured to absorb the solution and gasify the solution.

The filter cartridge of the air sterilizing device of the other embodiment of the disclosure comprises: a first tank, configured to contain the solution; a second tank; a diffusion pipe, connected with the pump and configured to supply the ozone to the lower portion of the first tank; a connection pipe, connected with the upper portion of the first tank and the lower portion of the second tank and configured to supply gas in the solution of the first tank to the second tank; and an evaporation part, configured to absorb the solution of the second tank and gasify the solution.

The tank comprises a groove for containing the ultrasonic generating unit.

The evaporation part is formed with one kind selected from a group of cellulose, paper and sponge.

The filter cartridge further comprises a film filter, and a through hole in the tank is coated by the film filter to allow the gas to pass through but not to allow the solution to pass through.

One part of the evaporation part is configured inside the tank, and the rest of the evaporation part is configured outside the tank.

In order to cover a large area of indoor space, the air sterilizing device of the disclosure generates a sufficient quantity of stable hydroxyl radicals by various reactions to realize a more excellent effect than the current art in the aspects of air purification and sterilization, thereby creating a comfortable living environment.

| Description of drawing reference numbers |
|---|
| 100: housing |
| 110: First flow path |
| 120: Second flow path |
| 130: Third flow path |
| 140: Photocatalysis substance |
| 200: ozone generating unit |
| 300: Filter cartridge |
| 310: Tank |
| 311: First tank |

| Description of drawing reference numbers |
|---|
| 312: Second tank |
| 330: Evaporation part |
| 360: Film filter |
| 400: ultrasonic generating unit |
| 500: Air supply fan |
| 700: Pump |
| 710: Ozone suction pipe |
| 720: Ozone supply pipe |

DETAILED DESCRIPTION

The disclosure is described in detail with embodiments as the focus as follows. However, the scope of the disclosure is not limited to the drawings or embodiments referred to in the following description. The drawings are merely exemplary selections for the purpose of specifying the disclosure in various embodiments.

In order to help understand the disclosure, the various structural elements and their shapes in the drawings will be simplified or enlarged, and the structural elements in actual products will be omitted instead of being all shown. Accordingly, the drawings shall be interpreted to enhance the understanding of the disclosure. On the other hand, the elements in the drawings that have the same effect are endowed with the same drawing reference numbers.

In the whole specification, when it is expressed that one part is "connected" to another, it includes not only "directly connected" cases, but also "electrically connected" cases where other devices are disposed in the middle. Moreover, when it is expressed that one part "comprises" a certain structural element, as long as no particular conflict is described, it means that one part further comprises other structural elements that are not excluded.

In this specification, the terms first, second, third and the like may be used in the description of various structural elements, but it does not mean that such structural elements are limited by the above-mentioned terms. The objective of the terms is to distinguish one structural element from another. For instance, without departing from the scope of the claims of the disclosure, the first structural element may be named as the second structural element or the third structural element, etc. Similarly, the second structural element or the third structural element may also be named interchangeably.

Furthermore, when it is recorded that a certain layer or structural element is located "above" another layer or structural element, it means that the certain layer or structural element is configured to make direct contact with another layer or structural element or the certain layer or structural element and another layer or structural element are configured with another layer disposed between them.

An air sterilizing device of one embodiment of the disclosure is described as follows in conjunction with the accompanying drawings.

Figure 1:
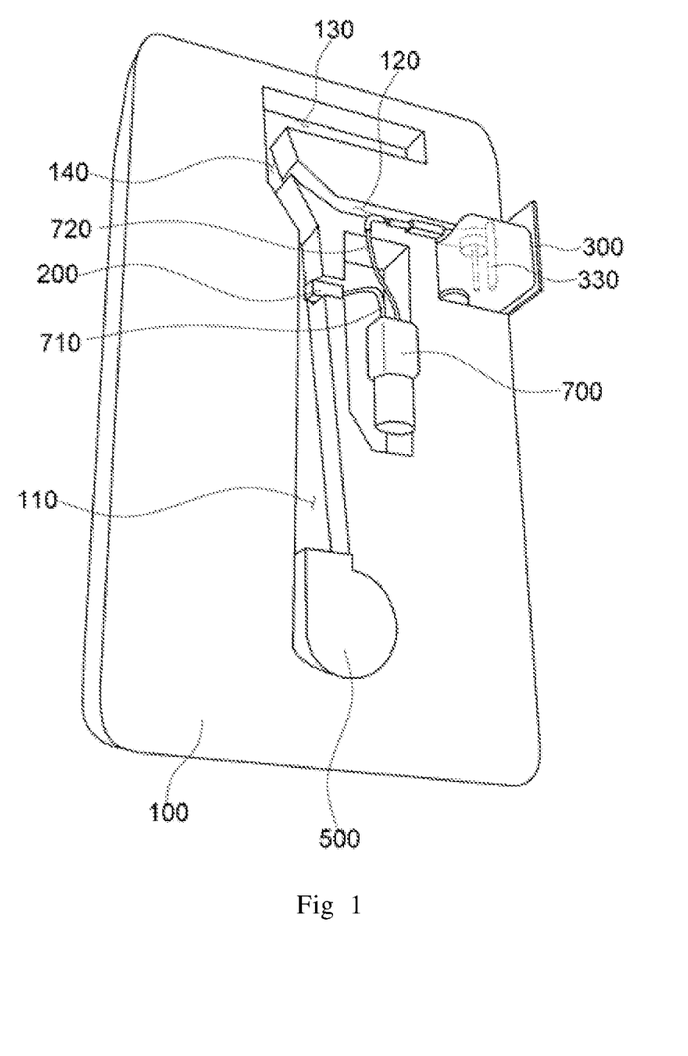
FIG. 1 is a sectional view of an internal structure of the air sterilizing device of one embodiment of the disclosure.
Figure 2:
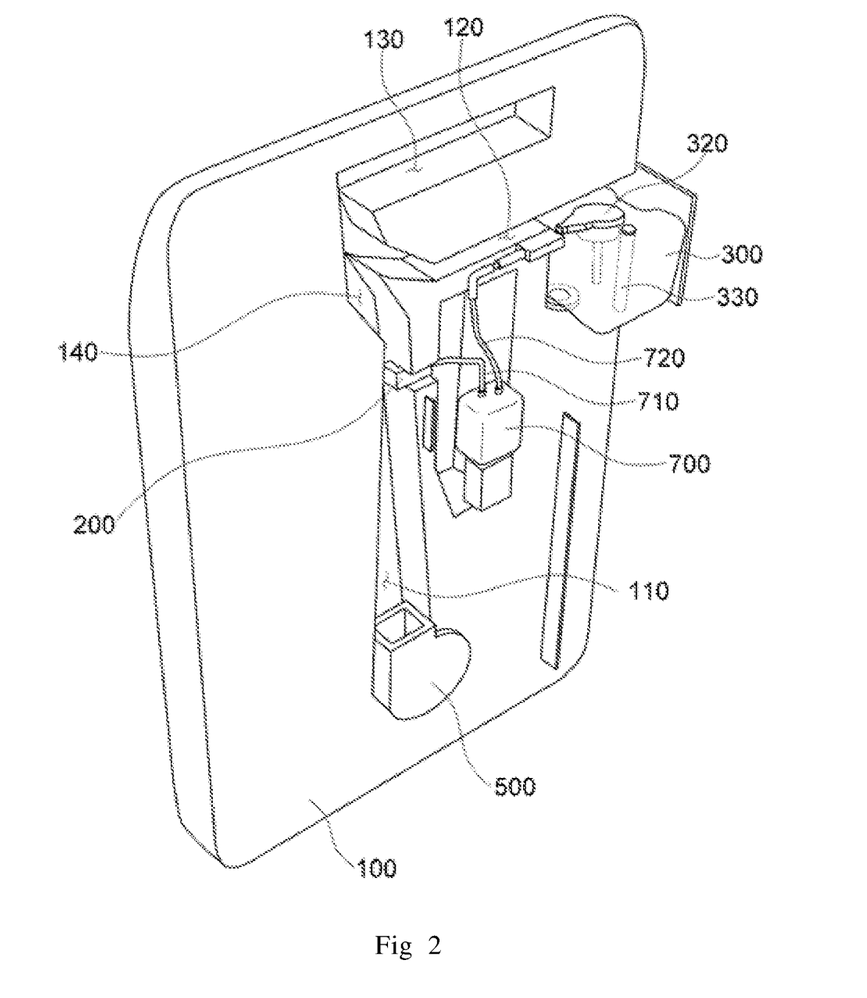
FIG. 2 is a perspective view of an upper side of an internal structure of the air sterilizing device of one embodiment of the disclosure observed from the upper side.
Figure 3:
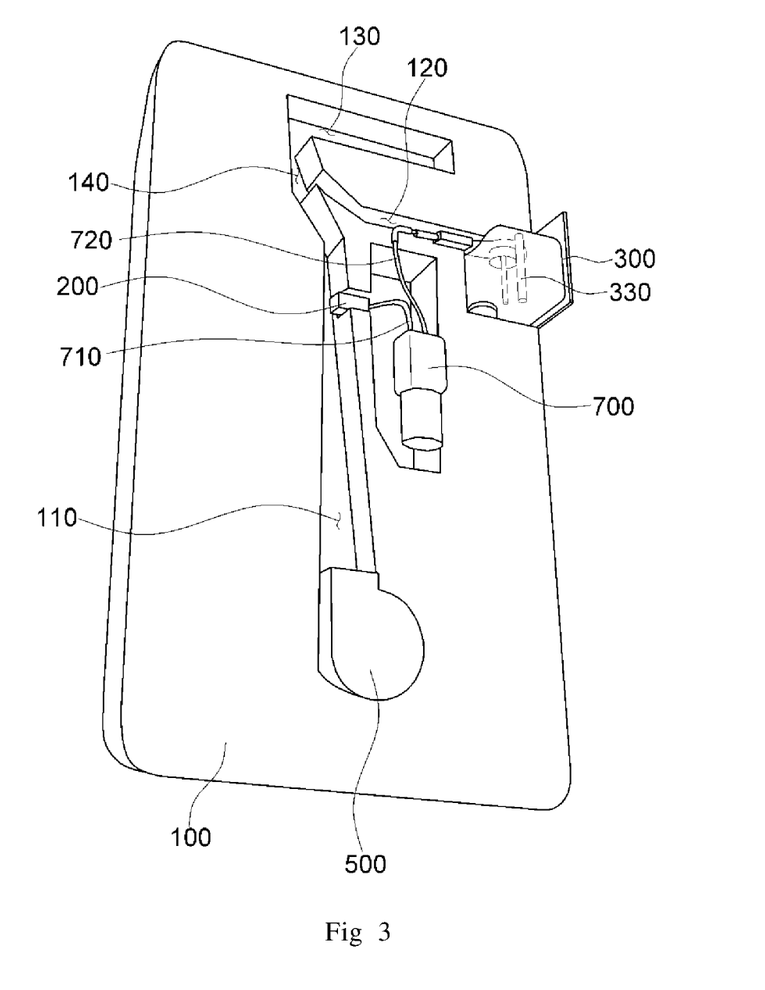
FIG. 3 is a perspective view of a lower side of an internal structure of the air sterilizing device of one embodiment of the disclosure observed from the lower side.
Figure 4:
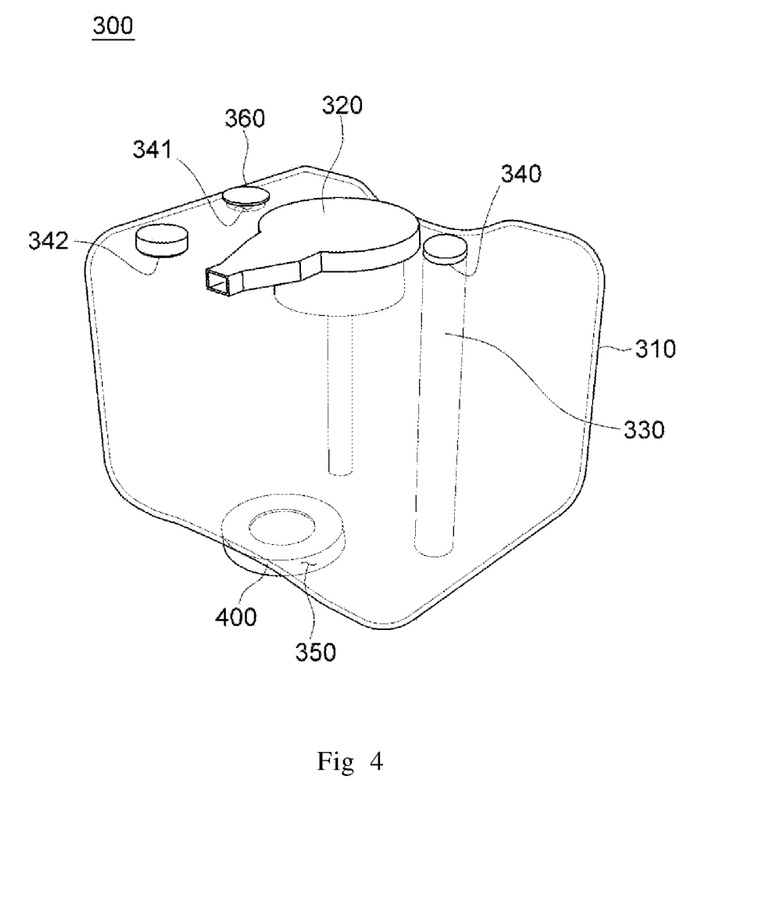
FIG. 4 is a perspective view of a filter cartridge of the air sterilizing device of one embodiment of the disclosure.

FIG. 1 is the sectional view of the internal structure of the air sterilizing device of one embodiment of the disclosure, FIG. 2 is the perspective view of the upper side of the internal structure of the air sterilizing device of one embodiment of the disclosure observed from the upper side, FIG. 3 is the perspective view of the lower side of the internal structure of the air sterilizing device of one embodiment of the disclosure observed from the lower side, and FIG. 4 is the perspective view of the filter cartridge of the air sterilizing device of one embodiment of the disclosure.

By reference to FIG. 1 to FIG. 4, the air sterilizing device of one embodiment of the disclosure comprises: a housing 100, forming an air flow path thereon; an ozone generating unit 200, generating ozone particles by electrodes to be supplied to the air flow path; a filter cartridge 300, receiving the ozone generated by the ozone generating unit 200 to discharge bubbles containing the ozone and hydroxyl radicals; an ultrasonic generating unit 400, connected to the filter cartridge 300 to generate ultrasonic waves; an air supply fan 500, configured to supply air to the air flow path of the housing 100; and a power supply unit (not shown), configured to supply power for driving the ozone generating unit 200, the ultrasonic generating unit 400 and the air supply fan 500.

The housing 100 comprises: the first flow path 110, configured to guide the air supplied by the air supply fan 500; a second flow path 120, configured to guide gas in the bubbles generated by deionized water in the deionized water filter cartridge; and a third flow path 130, configured to mix the air flowing in the first flow path 110 with the gas in the second flow path 120. Sectional areas of the first flow path 110 gradually decrease in the direction away from the air supply fan, and sectional areas of the second flow path 120 are partly constant but gradually increase in the direction close to the first flow path 110. Sectional areas of the third flow path 130 gradually increase in the direction away from the first flow path 110 and the second flow path 120. Air flows in the first flow path 110 in a form of Turbulent Flow and flows in the third flow path 130 in a form of Laminar Flow.

The air in the first flow path 110 sucks in the gas generated in the bubbles in the second flow path 120 by a Venturi effect.

A photocatalysis substance 140 (such as $TiO_2$) is coated on the inner wall of at least one of the second flow path 120 and the third flow path 130.

A light source (such as an ultraviolet light-emitting diode UV (Ultra Violet) LED) is configured on the second flow path 120 to illuminate the photocatalysis substance by ultraviolet light of less than 390 nm to react with hydrogen peroxide ($H_2O_2$) contained in the gas passing through the second flow path 120 and the third flow path 130 to generate the hydroxyl radical (2OH−).

The ozone generating unit 200 is connected with the first flow path 110 and supplies ozone generated by high voltage to the first flow path 110 all the time.

The air sterilizing device of one embodiment of the disclosure may comprise a pump 700 configured to supply one part of ozone generated by the ozone generating unit 200 into the filter cartridge 300.

The pump 700 sucks in one part of ozone generated by the ozone generating unit 200 through an ozone suction pipe 710 connected with the ozone generating unit 200 and supplies ozone to the filter cartridge 300 through an ozone supply pipe 720 connected with the filter cartridge 300.

The pump 700 only works for periods of time in the working process of the ozone generating unit 200. For instance, the pump only works for 5 min to 10 min every hour to supply ozone to the filter cartridge 300. Thus, sufficient hydrogen peroxide may be generated in the filter cartridge 300, to avoid that the yield of hydroxyl radicals is reduced by excessively supplying ozone into the filter cartridge 300.

By reference to FIG. 4, the filter cartridge 300 of one embodiment of the disclosure comprises: a tank 310, configured to contain the solution; a diffusion pipe 320, connected with the ozone supply pipe 720 and configured to supply the ozone into the solution; and an evaporation part 330, configured to absorb the solution, gasify the solution and allow the solution to flow towards the second flow path 120.

One part of the evaporation part 330 is exposed in the second flow path 120 outside the tank 310 through a first through hole 340 formed in the tank 310, and the rest of the evaporation part 330 is configured inside the tank 310.

The evaporation part 330 absorbs the solution and supplies one part of the solution at a gas state to the second flow path 120. The evaporation part 330 is made of a hygroscopic material, for instance, one kind selected from a group of cellulose, paper and sponge.

Moreover, the filter cartridge 300 may comprise a groove 350 formed in the tank 310 and configured to contain the ultrasonic generating unit 400.

The filter cartridge 300 may further comprise a film filter 360, and a second through hole 341 formed in the tank 310 is coated by the film filter 360 to allow the gas in the bubbles from the solution to pass through but not to allow the solution to pass through. The filter cartridge 300 may comprise a solution put-in port 342 configured to put in the solution and covered with a cover.

The solution of the filter cartridge 300 is deionized water (DI) or 1% hydrogen peroxide water. When the solution in the filter cartridge 300 is not sufficient, people may open the cover to supplement the deionized water or hydrogen peroxide water through the solution put-in port 342.

The film filter 360 may comprise a plurality of thin films made of polytetrafluoroethylene (ePTFE), with about 1.4 billion air pores/$cm^2$. For instance, GORE-TEX may serve as the film filter 360.

Figure 5:
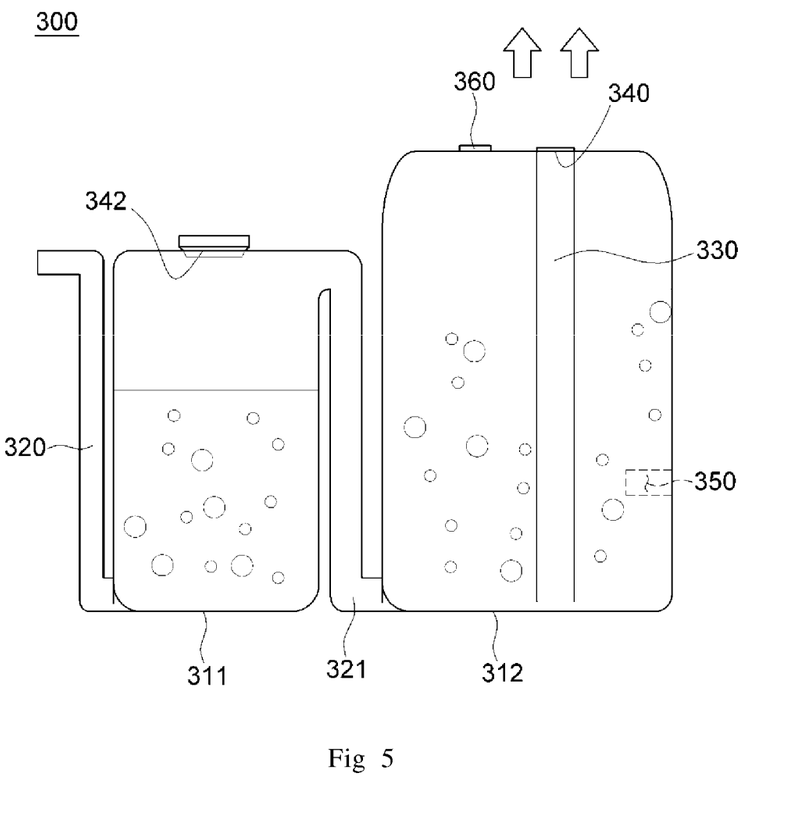
FIG. 5 is a perspective view of a filter cartridge of the air sterilizing device of the other embodiment of the disclosure.

By reference to FIG. 5, a filter cartridge 300 of the other embodiment of the disclosure comprises: a first tank 311 and a second tank 312, configured to contain a solution; a diffusion pipe 320, connected with an ozone supply pipe 720 and configured to supply the ozone to the lower portion of the first tank 311; a connection pipe 321, connected with the upper portion of the first tank 311 and the lower portion of the second tank 312 and configured to supply gas in the solution of the first tank 311 to the second tank 312; and an evaporation part 330, configured to absorb the solution of the second tank 312, gasify the solution and supply the solution into a second flow path 120.

One part of the evaporation part 330 is exposed in the second flow path 120 outside the tank 312 through a first through hole 340 formed in the second tank 312, and the rest of the evaporation part 330 is configured inside the second tank 312.

The evaporation part 330 absorbs the solution and supplies one part of the solution at a gas state to the second flow path 120. The evaporation part 330 is made of a hygroscopic material, for instance, the evaporation part 330 is formed with one kind selected from a group of cellulose, paper and sponge.

Moreover, the filter cartridge 300 may comprise a groove 350 formed in at least one of the first tank 311 and the second tank 312 and configured to contain an ultrasonic generating unit 400.

The filter cartridge 300 may further comprise a film filter 360, and a second through hole 341 formed in the second tank 312 is coated by the film filter 360 to allow the gas in bubbles from the solution to pass through but not to allow the solution to pass through. The filter cartridge 300 may comprise a solution put-in port 342 configured to put the solution into at least one of the first tank 311 and the second tank 312 and covered with a cover.

The ultrasonic generating unit 400 is inserted in the groove 350 of the filter cartridge 300 to generate ultrasonic waves. The ultrasonic generating unit 400 decomposes the water that serves as the solution by exerting the ultrasonic waves on the solution in the tank so as to generate radicals such as OH⁻ and H⁺. The ultrasonic generating unit 400 generates the ultrasonic waves with a frequency of 15 Khz to 10 MHz so as to weaken frameworks of pillbug, yeast and enzyme.

By reference to the accompanying drawings, the action of generating the hydroxyl radical by the air sterilizing device of one embodiment of the disclosure is described as follows.

Table 1 describes a generation principle of the hydroxyl radical generated by the air sterilizing device of the disclosure.

Two reactions represented by one Formula as follows, $$2O_3+H_2O \rightarrow 2O_2+OH^-+HO_2^+, \text{ and}$$

$$HO_2^++O_2 \rightarrow 2O_2+OH^- \rightarrow 3O_3+H_2O \rightarrow 4O_2+2OH^- \quad \text{Formula 3:}$$

The filter cartridge 300 generates the hydroxyl radicals by two chain reactions.

First of all, the ozone and the water react to generate hydrogen peroxide and oxygen. Then, the generated hydrogen peroxide and the ozone react to generate two types of radicals OH⁻ and HO₂⁺. Under the condition that desalted water that serves as the solution in the filter cartridge 300 contains 1% of hydrogen peroxide, the two types of radicals and oxygen are more rapidly generated by reacting with the ozone supplied into the filter cartridge 300.

On the other hand, under the condition that the ozone and air flow into the filter cartridge, the air containing nitrogen

TABLE 1

|  | Ultravoilet light | TiO₂ (ultraviolet light of less than 387 nm) | O₃ | O⁻ | Ultrasonic decomposition | H⁻ | H⁺ |
|---|---|---|---|---|---|---|---|
| H₂O₂ | 2OH⁻ (less than 254 nm) | 2OH⁻ | OH⁻ + O₂ + HO₂⁺ | — | OH⁻ + H⁺ | — | H₂O₂ |
| H₂O | H⁺ + OH (less than 190 mm) | H₂O₂ | OH⁻ + O₂ + HO₂⁺ | H₂O₂ | OH⁻ + H⁺ | H₂O₂ | H₂O |
| O₃ | O₂ + O⁻ | — | — | O₂ | — | H⁻ + O₂ | O₃ |
| O₂ | O⁻ + O⁻ | H₂O₂ | — | O₃ | O⁻ + O⁻ | HO₂⁺ | — |
| TiO₂ | 2OH⁻ | — | — | — | O⁻ + O⁻ | — | — |

By reference to FIG. 1 to FIG. 4, the filter cartridge 300 contains the solution such as deionized water supplied through the solution put-in port 342. The pump 700 sucks in one part of ozone generated by the ozone generating unit 200 through the ozone suction pipe 710 and supplies ozone to the filter cartridge 300 through the ozone supply pipe 720.

The ozone supplied to the filter cartridge 300 is dissolved in the deionized water that serves as the solution at a solubility of 570 mg/L at 20° C. When the pump 700 supplies the ozone into the filter cartridge 300 at a speed of 3 mg/hr and the ozone is subjected to foaming for 10 mins with the deionized water that serves as the solution of the filter cartridge 300, the volume of the ozone that enters the solution reaches 0.5 mg. When the volume of the solution in the filter cartridge 300 is 50 mL, the volume of the ozone in the solution reaches 0.5 mg, that is, 0.01 mg of ozone is dissolved in each 1 mL of solution and 0.01 g of ozone is dissolved in each 1 L of water.

When the ozone is supplied into the solution for 20 min at 20° C., 0.25 mg of ozone is dissolved in the solution. In this case, when the volume of the solution in the filter cartridge 300 is 50 mL, a concentration of the ozone dissolved in the solution reaches 0,005 mg/ml. 20 minutes later, the concentration of the ozone is halved to reach 0.0025 mg/mL; 20 more minutes later, the concentration of the ozone is halved again to reach 0.00125 mg/mL, that is, 1 hour later, the concentration of the dissolved ozone reaches 1.25 mg/L. Such ozone of such concentration is enough to react with water to generate hydrogen peroxide.

The ozone reacts with the water to generate the hydroxyl radicals by Formulas as follows.

$$O_3+H_2O \rightarrow H_2O_2+O_2 \quad \text{Formula 1:}$$

$$O_3+H_2O_2 \rightarrow OH^-+HO_2^++O_2 \quad \text{Formula 2:}$$

and the ozone may have different reactions in the solution. First, nitrogen and impurities are oxidized in the solution of the filter cartridge 300 to form nitric acid to be dissolved. Then, the ozone and water react to generate oxygen and the hydroxyl radicals according to Formulas.

By reference to FIG. 5, the filter cartridge 300 of the other embodiment of the disclosure comprises: the first tank 311 and the second tank 312, configured to contain the solution; the diffusion pipe 320, connected with the ozone supply pipe 720 and configured to supply the ozone to the lower portion of the first tank 311; the connection pipe 321, connected with the upper portion of the first tank 311 and the lower portion of the second tank 312 and configured to supply gas in the solution of the first tank 311 to the second tank 312; and the evaporation part 330, configured to absorb the solution of the second tank 312, gasify the solution and supply the solution into the second flow path 120.

First of all, the pump 700 sucks in one part of the ozone generated by the ozone generating unit 200 through the ozone suction pipe 710 and supplies the ozone to the first tank 311 of the filter cartridge 300 through the ozone supply pipe 720 connected with the filter cartridge 300 so as to generate bubbles. The nitrogen and impurities react with the ozone to dissolve the oxidized substances in the deionized water that serves as the solution of the first tank 311 to generate nitric acid.

Then, the clean ozone discharged out of the first tank 311 is supplied into the second tank 312 through the connection pipe 321. The ozone with the impurities removed reacts with the water in the second tank 312 to generate oxygen and the hydroxyl radicals (2O₂+OH⁻+HO₂⁺).

In this way, as shown in Table 1, the hydroxyl radicals (O₂+OH⁻+HO₂⁺) are generated by the ozone, hydrogen peroxide and deionized water in the filter cartridge 312 (by reference to the radicals recorded in the first line of the third row and the second line of the third row).

Then, the evaporation part 330 of the filter cartridge 300 supplies the solution to the second flow path 120 by absorbing vapor (and/or hydrogen peroxide).

Moreover, the film filter 360 of the filter cartridge 300 supplies oxygen, ozone and radicals ($OH^-$, $H^+$, $O^-$ and $HO_2^+$) generated in bubbles of the solution through the second through hole 341, to the second flow path 120.

The vapor (and/or hydrogen peroxide), oxygen and ozone that are supplied to the second flow path 120 react with the light source (such as the UV LED) through the photocatalysis substance 140 (such as $TiO_2$) to generate the hydroxyl radical ($2OH^-$) (by reference to the radicals recorded in the first row and the second row of Table 1).

The air supply fan 500 mixes the air supplied into the first flow path 110 with the ozone discharged out of the ozone generating unit 200. The air mixed with the ozone when passing through the first flow path 110 realizes the Venturi effect when passing through the second flow path 120 so as to be mixed with the vapor (and/or hydrogen peroxide), ozone and hydroxyl radicals in the second flow path 120 and supplied to the third flow path.

The vapor (and/or hydrogen peroxide) and ozone supplied to the third flow path 130 react with the light source (such as the UV LED) through the photocatalysis substance 140 (such as $TiO_2$) to generate the hydroxyl radical ($2OH^-$) (by reference to the radicals recorded in the first row and the second row of Table 1).

On the other hand, the ultrasonic generating unit 400 inserted in the groove 350 of the filter cartridge 100 generates ultrasonic waves to decompose the water in the filter cartridge 300 so as to generate radicals such as $OH^-/H^+$ and vibrates vapor (and/or hydrogen peroxide) in the first flow path 110, the second flow path (120) and the third flow path (130) to generate the hydroxyl radicals (by reference to the radicals recorded in the sixth row of Table 1).

The hydroxyl radicals generated in the aforementioned process together with air are discharged out of the third flow path 130.

The air sterilizing device of the disclosure generates ozone in the ozone generating unit 200, but a concentration of the ozone discharged out of the third flow path 130 is controlled within a hazard control range of 0.001 ppm to 0.05 ppm according to the regulation of UL 867.

Particularly, the ozone generated in the ozone generating unit 200 reacts with the solution in the filter cartridge 300 and the ultraviolet light by the physical-chemical chain reactions. The ultrasonic generating unit 400 decomposes water molecules and generates resonance. The ozone is diluted with the air supplied by the air supply fan 500, and the concentration of the ozone may be sufficiently reduced by reactions of the ultraviolet light source and the photocatalysis substance.

The air supply fan 500 and the ozone generating unit 200 are adjusted by making the ozone reach a range of 0.0001 g to 0.5 g at the position 5 cm away from the third flow path 130 of the air sterilizing device of the disclosure. Gasification is performed by adjusting a wind velocity of the air supply fan 500 and making a quantity of hydrogen peroxide reach a range of 0.001 g to 0.5 g, and this adjustment is made by discharging 500,000 to 20,000,000 hydroxyl radicals per cc.

According to a standard concentration reference (WEL) of the hydroxyl radicals, the number of the hydroxyl radicals generated by 1.4 $mg/m^3$ (1 ppm) hydrogen peroxide is (1.4 $mg/m^3$)/(34 g/mol)=0.0000411 $moles/m^3$.

As 0.0000411 $moles/m^3 \times 6.23 \times 10^{23} = 2.56 \times 10^{19}$ molecules/$m^3$, if one hydrogen peroxide molecule generates two hydroxyl radical molecules, then the maximum discharge of the hydroxyl radicals is $2.56 \times 10^{19} \times 2 = 5.12 \times 10^{19}/m^3$, namely $5.12 \times 10^{13}$/ml.

The number of the hydroxyl radicals that the air sterilizing device of the disclosure may generate through the hydrogen peroxide is (0.008 mols)$\times(6.023 \times 10^{23}) \times 2 = 9.63 \times 10^{23}$. If the air sterilizing device continuously works for 60 days, the number of the hydroxyl radicals that may be acquired every day in average is $1.6 \times 10^{20}$.

When a space for configuring the air sterilizing device of the disclosure is set to be 300 $m^3$ large, the number of the hydroxyl radicals generated through the hydrogen peroxide is $1.6 \times 10^{20}$ radicals/1 day/300 $m^3 = 5.33 \times 10^{17}$ radicals/1 $m^3$/1 day, that is equivalent to $5.33 \times 10^{11}$ mL/day, which is far lower than the standard discharge limit.

Thus, the air sterilizing device of the disclosure generates a large number of hydroxyl radicals through ozone generated by various ways.

The ozone generating unit 200 generates ozone through the ceramic electrodes driven by a high-voltage circuit and a controller, the generated ozone is led into the filter cartridge 300 through the pump 700 to generate bubbles in the filter cartridge 300. Moreover, in order to supplement the yield of the hydroxyl radicals based on the hydrogen peroxide by the reactions between the ozone and the water, the ozone generating unit 200 continuously supplies the ozone to the first flow path 110. In addition, the ozone is also generated in the filter cartridge 300.

On the other hand, if $O^-$ radicals, oxygen molecules and ozone sucked in the air flow in the second flow path 120 converge in the second flow path 120 and the third flow path 130 that serve as reaction spaces for the photocatalysis substance and the LED light source, the ozone and hydrogen peroxide water generated in the filter cartridge 300 have a better effect on generating the hydroxyl radicals. In addition, the air Turbulent Flow generated in the second flow path 120 and the third flow path 130 that serve as the reaction spaces is beneficial for mixing the ozone with the hydrogen peroxide sufficiently.

In order to help generate all the hydroxyl radicals, the ultrasonic generating unit 400 converts electric energy into mechanical energy to exert ultrasonic waves on the filter cartridge 300. By exerting the ultrasonic waves in the filter cartridge 300, the physical-chemical reactions are generated to decompose water into a strong oxidizer for radicals such as $OH^-/H^+$.

The acquired radicals react with a group of other radicals (radicals generated through the chain reactions between the ultraviolet light of less than 390 nm and the vapor, oxide water, ozone, oxygen and the like that flow together with the air flow into the second flow path 120 and the third flow path 130 subjected to vapor deposition of the photocatalysis substance $TiO_2$) generated in the decomposition process of the ozone, and the hydroxyl radicals generated are jet into the air.

The air sterilizing device of the disclosure discharges the generated hydroxyl radicals together with anions out of the third flow path 130 in a form of Laminar Flow so as to discharge them to a space as widely as possible.

In addition, the air sterilizing device of the disclosure works under the condition that a residual volume of the solution or water in the filter cartridge 300 exceeds a specified value. Otherwise, it does not work but displays a warning sign.

Therefore, though not shown in accompanying drawings, the filter cartridge 300 of the air sterilizing device of the disclosure may further comprise a light source, a reflection part and a sensing part disposed on the reflection part, and the sensing part detects the light that is sent out by the light source and reflected by the reflecting part.

If the light goes back and forth in the solution or water in the filter cartridge, its quantity decreases. In this case, the quantity of the light received by the sensing part increases, so people are reminded to supplement the solution or replace the filter cartridge.

Although the disclosure has been disclosed as above in preferred embodiments, it is not intended to limit the disclosure. Various modifications and variations can be made by those skilled in the art without departing from the protection scope of the disclosure. Thus, the protection scope of the disclosure should be defined by Claims.

What is claimed is:

1. An air sterilizing device, comprising:
    a housing, configured to form air flow paths;
    an ozone generating unit, generating ozone particles to be supplied to the air flow path;
    a filter cartridge, receiving ozone generated by the ozone generating unit to discharge bubbles containing ozone and hydroxyl radicals;
    an ultrasonic generating unit, connected to the filter cartridge to generate ultrasonic waves;
    an air supply fan, configured to supply air to a first air flow path of the housing;
    a power supply unit, configured to supply power for driving the ozone generating unit, the ultrasonic generating unit and the air supply fan; and
    a pump connected with the ozone generating unit and configured to supply part of the ozone particles to the filter cartridge;
    wherein the filter cartridge comprises:
    a first tank, configured to contain a solution;
    a second tank;
    a diffusion pipe, connected with the pump and configured to supply the ozone to the lower portion of the first tank;
    a connection pipe, connected with the upper portion of the first tank and the lower portion of the second tank and configured to supply gas in the solution of the first tank to the second tank; and
    an evaporation part, configured to absorb the solution of the second tank and gasify the solution.

2. The air sterilizing device according to claim 1, wherein the housing comprises:
    the first flow path, configured to guide the air supplied by the air supply fan;
    a second flow path, configured to guide gas in the bubbles generated by the solution in the filter cartridge; and
    a third flow path, configured to mix the air flowing in the first flow path with the gas in the second flow path.

3. The air sterilizing device according to claim 1, wherein the pump only works for periods of time in the working process of the ozone generating unit.

4. The air sterilizing device according to claim 1, wherein the first tank or the second tank comprises a groove for containing the ultrasonic generating unit.

5. The air sterilizing device according to claim 1, wherein the evaporation part is formed with one selected kind from a group of cellulose, paper, and sponge.

6. The air sterilizing device according to claim 1, wherein the filter cartridge further comprises a film filter, and a through hole in the second tank is coated by the film filter to allow the gas to pass through but not to allow the solution to pass through.

7. The air sterilizing device according to claim 1, wherein one part of the evaporation part is configured inside the second tank, and the rest of the evaporation part is configured outside the second tank.

8. The air sterilizing device according to claim 1, wherein at least one of the first tank and the second tank comprises a groove for containing the ultrasonic generating unit.

9. The air sterilizing device according to claim 1, wherein the filter cartridge further comprises a film filter, and a through hole in the second tank is coated by the film filter to allow the gas to pass through but not to allow the solution to pass through.

10. The air sterilizing device according to claim 1, wherein one part of the filter cartridge is configured inside the second tank, and the rest is configured outside the second tank.

11. The air sterilizing device according to claim 1, wherein the ultrasonic generating part generates ultrasonic waves at a frequency of 15 Khz to 10 Mhz.

* * * * *